(12) United States Patent
Wester et al.

(10) Patent No.: US 8,192,769 B2
(45) Date of Patent: Jun. 5, 2012

(54) PROTEIN HYDROLYSATE AND PLANT STEROL CONTAINING COMPOSITION FOR IMPROVING SERUM LIPID PROFILE AND PREVENTING ATHEROSCLEROSIS

(75) Inventors: Ingmar Wester, Turku (FI); Paivi Kuusisto, Naantali (FI)

(73) Assignee: Raisio Nutrition Ltd., Raisio (FI)

(*) Notice: Subject to any disclaimer, the term of this patent is extended or adjusted under 35 U.S.C. 154(b) by 0 days.

(21) Appl. No.: 13/210,250

(22) Filed: Aug. 15, 2011

(65) Prior Publication Data

US 2011/0301085 A1 Dec. 8, 2011

Related U.S. Application Data

(63) Continuation of application No. 12/621,312, filed on Nov. 18, 2009, now abandoned, which is a continuation of application No. 10/498,519, filed as application No. PCT/FI02/01053 on Dec. 20, 2002, now abandoned.

(30) Foreign Application Priority Data

Dec. 21, 2001 (FI) ..................................... 20012553

(51) Int. Cl.
*A61K 36/00* (2006.01)
*A61K 36/48* (2006.01)
*A61K 38/00* (2006.01)

(52) U.S. Cl. ........................ 424/757; 424/725; 514/7.4

(58) Field of Classification Search .................. None
See application file for complete search history.

(56) References Cited

U.S. PATENT DOCUMENTS

| | | | |
|---|---|---|---|
| 5,523,087 | A | 6/1996 | Shlyankevich |
| 6,063,776 | A | 5/2000 | Ostlund, Jr. |
| 6,113,972 | A | 9/2000 | Corliss et al. |
| 6,303,178 | B1 | 10/2001 | Tsumura et al. |
| 6,316,041 | B1 | 11/2001 | Stock et al. |
| 6,579,534 | B2 | 6/2003 | Waggle et al. |
| 2001/0006672 | A1 | 7/2001 | Akashe et al. |
| 2006/0121176 | A1 | 6/2006 | Mozaffar |

FOREIGN PATENT DOCUMENTS

| | | |
|---|---|---|
| EP | 0 626 175 | 11/1994 |
| EP | 1 046 396 | 10/2000 |
| EP | 1121928 A1 | 8/2001 |
| JP | 60 114252 | 1/1985 |
| JP | 03076557 A | 4/1991 |
| JP | 05070323 A | 3/1993 |
| JP | 9157179 | 6/1997 |
| JP | 2000344676 A | 12/2000 |
| WO | WO/0030665 | 6/2000 |
| WO | WO-0132029 A2 | 5/2001 |
| WO | WO/0137681 | 5/2001 |

OTHER PUBLICATIONS

Navari-Izzo et al.; Sterol evolution in field-grown soybean plants (Glycine max (L.) Merr.) influenced by sunlight filtered through different poly(vinyl chloride) filters. Agrochimica (1982); 26(4); 376-89.
Tripathi et al.; Soybean—a consummate functional food: A review. Journal of Food Science and Technology (2005); 42(2); 111-119.
Aoyama et al., Soy protein isolate and its hydrolysate reduce body fat of dietary obese rats and genetically obese mice (Yellow KK); Nutrition 16: 349-354; 2000.
Sugano, Michihiro et al.; "Cholesterol-Lowering Activity of Various Undigested Fractions of Soybean Protein in Rats"; J. Nutr.; 1990; 120 (9); 977-985.
English language translation of Notification of Reasons for Refusal dated Feb. 24, 2009, from corresponding Japanese Application No. 2003-555906.
Tanaka et al. "Effect of partial hydrohyzates of casein and soybean protein on serum lipoproteins and fecal neutral steroids", J. Nutr Sci Vitaminol, 1983, 29: 439-446.

*Primary Examiner* — Qiuwen Mi
(74) *Attorney, Agent, or Firm* — Arent Fox LLP

(57) ABSTRACT

The invention relates to a terapeutical composition comprising a protein hydrolysate and a plant sterol, wherein the weight ratio of the plant sterol to the protein hydrolysate is from 1:0.02 to 1:150. The invention also relates to a terapeutical composition comprising a protein hydrolysate and a synthetic emulsifier and/or a lipid based gain fraction having emulsifying properties. Said compositions can be used in a pharmaceutical, nutraceutical or food product for improving serum lipid profile.

16 Claims, No Drawings

PROTEIN HYDROLYSATE AND PLANT STEROL CONTAINING COMPOSITION FOR IMPROVING SERUM LIPID PROFILE AND PREVENTING ATHEROSCLEROSIS

CROSS-REFERENCE TO RELATED APPLICATION

This application is a continuation of U.S. application Ser. No. 12/621,312, filed Nov. 18, 2009, which is a continuation of application Ser. No. 10/498,519, filed Oct. 1, 2005, now abandoned, which is a National Stage Entry of International Application No. PCT/FI2002/001053, with an international filing date of Dec. 20, 2002, which claims priority to Finland Patent Application No. 20012553, filed Dec. 21, 2001. These prior applications are hereby incorporated by reference herein in their entirety.

FIELD OF INVENTION

The present invention relates to the field of nutrition and health. Especially it concerns improved compositions for oral use suitable for improving serum lipid profile including reducing serum total and/or LDL cholesterol and/or apolipoprotein B levels.

BACKGROUND OF THE INVENTION

Cardiovascular disease (CVD) is one of the major causes of death in western world.

Elevated serum total and/or LDL (low density lipoprotein) cholesterol and triacyl-glycerol levels, as well as low ratio of HDL (high density lipoprotein) cholesterol to LDL cholesterol, are some of the major risk factors for CVD. Recently also serum levels of apolipoprotein B 100 (apo B) has been shown to be a reliable CVD risk marker. In most developed countries a substantial amount of the population have serum cholesterol levels not within the recommended levels. One of the first steps in improving the serum lipid profile is changes in life style including changes in diet and exercise. It seems, however, difficult to change dietary habits and to follow dietary recommendations. Thus, there is a clear need for solutions beyond regular diet and lifestyle changes by which serum lipid profile can be improved.

Food products enriched with components having cholesterol lowering effect beyond normal nutrition have been commercially available for some time. Representative examples are food products enriched with plant stanol or sterol fatty acid esters. Stanol fatty acid esters and the cholesterol lowering effects thereof are disclosed in U.S. Pat. No. 5,502,045 as well as a suitable method for their preparation. Dietary intake of 2 to 3 g/day of plant stanols is reported to lower serum LDL cholesterol levels in man up to 14% without affecting HDL cholesterol levels. The amount of atherogenic apolipoprotein B particles in blood is also decreased, thus reducing the risk of CVD.

Some proteins have also been used to improve serum lipid profile. Proteins that have been shown to lower serum total and/or LDL cholesterol include e.g. soy protein (Anderson J. W., et al, New Engl. J. Medicine 1995 333 (5) 276-282), whey protein (Nagaoka et al., Agric. Biol. Chem. 1991 (55) 813-818) and wheat gluten (EP 0 790 060 A1). FDA has approved a health claim about the role of soy protein in reducing the risk of CVD by lowering blood cholesterol levels. In order to qualify for this health claim, a food must contain at least 6.25 grams of soy protein per serving, the amount being one-fourth of the effective level of 25 grams per day, and be included in a diet low in saturated fat and cholesterol.

EP 0 669 835 B1 describes a hypocholesterolemic dietary composition containing soy protein and sitosterols, the sitosterols and soy protein being of natural origin and having synergistic cholesterol lowering effect. The composition is used for example as tablets, capsules or syrups. Effective daily intakes of the composition are not given Also EP 1 046 396 A2 describes a composition containing soy protein, preferably soy protein isolate or soy protein concentrate, and plant sterols having synergistic cholesterol lowering effect. The synergistic effect is achieved, when both the soy protein and plant sterols are administered in amounts that would be sufficient to induce cholesterol-lowering activity of each of the administered compound alone. WO 01/37681 describes a composition containing phytosterols and an isolated water-soluble protein, such as soy protein or caseinate, and optionally also an emulsifier. The composition can be utilized in food products, where the composition improves mouthfeel and stability of the sterol containing foods. No improved cholesterol lowering effect compared to the effect achieved with phytosterols alone is attributed to this composition.

U.S. 6,113,972 describes a phytosterol protein complex, where the complex increases the bioavailability of the phytosterols. No cholesterol lowering effect is attributed to the protein part of this composition, but the protein functions only as a carrier to the phytosterols. In fact, any fat binding protein can be used in this complex and especially egg proteins are preferred. A composition containing plant sterols/stanols and an emulsifier, mixed into a protein-containing product, is described in WO 00/33669. The protein does not have any cholesterol lowering effect in this composition either, but it aids in the formation of the emulsion.

Protein hydrolysates have been shown to have greater serum cholesterol lowering effect than the corresponding unhydrolyzed proteins (Sugano et al., J. Nutr. 1990 (120) 977-985). The cholesterol lowering effect of protein hydrolysates might be attributed to certain peptides, for example such as found from bovine milk β-lactoglobulin by Nagaoka et al. (Biochem. Biophys. Res. Commun., 2001, 281(1), 11-17), but this still remains to be proven by well-controlled clinical and/or animal studies. EP 0 790 060 A1 discloses a protein hydrolysate/phospholipid complex for improving lipid metabolism, where the complex contains 10% or more bound phospholipids, especially lecithin or enzyme modified lecithin. Lipid profile improving effect, especially LDL-cholesterol lowering and HDL-cholesterol raising effect of lecithin is well known in prior art (for example Childs et al., 1981, Atherosclerosis 38, 217). In the complex according to EP 0 790 060 A1 certain bound phospholipids (lecithin or enzyme modified lecithin) are believed to remarkably contribute to the lipid metabolism improving effect of the complex.

The current literature and especially FDA's interim approval of a health claim for plant sterols have increased the interest of the food industry in supplementing foods with plant sterols. Indeed, many such food items have recently been introduced into the market. It is assumed that new plant sterol containing foods will appear into the market rapidly.

The active launching of new plant sterol containing foods has raised a concern that a part of the population may have higher daily intake of plant sterols than what is needed to obtain an optimal cholesterol lowering effect. Short-term high intake of plant sterols has not been shown to be harmful. However, there is no data on possible long-term side effects of ingestion of high daily amounts (>3g/day or higher) of plant sterols. Furthermore, there is currently not a clear understanding of the biological impact of the increased serum level and thus higher systemic availability of plant sterols caused by increased intake from sterol enriched foods, especially foods enriched with unsaturated plant sterols.

There is a clear need for improved solutions by which the serum lipid profile can be improved, e.g. elevated serum total and/or LDL cholesterol levels reduced and/or HDL cholesterol levels increased and/or triacylglycerol levels reduced and/or apolipoprotein B levels reduced. Compositions based on combinations of active ingredients having enhanced, additive or even synergistic effects compared to the active ingredients alone are needed. It would also be desirable to obtain meaningful and sustainable improvements in the serum lipid profile with lower daily intake of the individual active ingredients than what is obtainable with the intakes currently used. Possible adverse effects of the active ingredients such as possible impact on fat-soluble antioxidants and other digestive discomforts could thus be reduced. Incorporation of the active ingredients into a wider range of food products without adverse effects on organoleptic properties is also needed. The present invention provides compositions meeting these requirements.

SUMMARY OF THE INVENTION

The present invention provides improved compositions for improving serum lipid profile in humans and/or animals and a method for improving serum lipid profile in humans and/or animals by orally administering the composition. In one aspect the compositions comprise combinations of protein hydrolysates and plant sterols. The compositions may optionally comprise also emulsifier(s) and/or fat and/or mineral salt. The compositions comprise one or more protein hydrolysates in combination with one or more plant sterols (sterols and/or stanols) in their free and/or esterified forms, optionally in combination with one or more emulsifiers and/or fat and/or mineral salt. Preferably the emulsifier is used to produce a complex with protein hydrolysates and/or sterols. In a second aspect the compositions comprise combinations of protein hydrolysates and synthetic emulsifier(s). The compositions may optionally comprise also fat and/or mineral salt. In a third aspect of the invention the compositions comprise combinations of protein hydrolysates and lipid based grain fractions having emulsifying properties. The compositions may optionally comprise also fat and/or mineral salt.

The compositions can be used as such or as pharmaceuticals or nutraceuticals or most advantageously in food products. Typically such an improved composition is a complex containing soy protein hydrolysate, emulsifier and plant sterols, advantageously used in food products for improving the serum lipid profile.

It was found that the combination of protein hydrolysates and plant sterols, optionally with emulsifiers and/or fat and/or mineral salt, further enhance the serum lipid profile improving effect that is obtained by using the individual active ingredients and even work synergistically in improving the overall serum total lipid profile, for instance in reducing blood serum total and/or LDL cholesterol levels, and have greater effect than the additive effect that was expected. In addition some of the combinations, especially those containing soy protein hydrolysate showed beneficial effect on HDL cholesterol levels. Also the lowering of serum triglyceride levels was shown to be surprising effective.

The present invention provides also means for further improving of serum lipid profile by using combinations of the active ingredients compared to the effects obtained when one of the ingredients is used alone. For example using the compositions of the present invention in combination with a healthy recommended diet provides means by which serum LDL cholesterol level can be reduced even by 25% or more. The present invention thus provides a versatile non-drug approach to improve serum lipid profile, e.g. to lower serum total and/or LDL cholesterol, especially in subjects having serum lipid levels not within the recommended limits. The present invention also provides combinations of the active ingredients, especially those containing mineral salt and/or specific protein hydrolysates, that have beneficial effect on blood pressure. The combination of the active ingredients according to the present invention thus reduces the risk of CVD beyond what is obtainable by using only one of the active ingredients.

The present invention further provides means for minimizing the daily intake of plant sterols in humans and still achieving a similar serum lipid profile improving effect as obtained with recommended daily intake of plant sterols from commercial plant sterol enriched products. This is especially important as the daily amount of plant sterols needed for obtaining a reduction in serum total and/or LDL cholesterol can be reduced, thus preventing potential over-consumption of plant sterols. Furthermore, the commercial availability of plant sterols is limited. In addition the commercial crude plant sterols are expensive due to their limited availability, whereas the availability of raw materials for protein hydrolysates or protein hydrolysate complexes usable according to this invention is not restricted.

By the use of the compositions according to the present invention the plant sterol supply can be more effectively utilized with the aim of reducing the risk of CVD in subjects as well as in the whole population. The present invention provides a way of obtaining an enhanced serum lipid profile improvement or a similar lipid profile improvement as obtained with plant sterols or protein hydrolysate based ingredients alone, but especially with lower daily intake of plant sterols and/or protein hydro-lysate. As active ingredients based on protein hydrolysates are cheaper than plant sterols the present invention also provides a way of obtaining an optimal lipid profile improving effect more cost effectively.

Compared to combinations of plant sterols and unhydrolyzed proteins previously known in the art, the compositions of the present invention comprising the combination of plant sterols and protein hydrolysates, optionally with emulsifiers and/or fat and/or mineral salt, have enhanced serum lipid profile improving effect and can also be utilized in a wider range of food products and by a wider range of consumers. In addition to having greater cholesterol lowering effect compared to unhydrolyzed proteins, protein hydrolysates are also less allergenic than unhydrolyzed proteins, thus enabling wider range of consumers being able to benefit the serum lipid profile improving effect. The compositions of the present invention can also be more easily incorporated into food products, such as beverages, without adverse effects on the texture due to the reduced viscosity of some of the protein hydrolysates compared to unhydrolyzed proteins.

A problem encountered with protein hydrolysates and their incorporation into food products is often a pronounced bitter taste of the hydrolysate. The bitter taste is the result of cleavage of the proteins at amino acids with hydrophobic side chains, which results in formation of peptides with exposed hydrophobic amino acid residues. Hydrolysates may thus have an adverse effect on the taste of the food product where they are incorporated. In addition to protein hydrolysates, also some protein hydrolysate/phospholipid complexes have bitter taste and can adversely affect the taste of the products containing them. In addition to off-flavors, some protein hydrolysate/phospholipid complexes, especially complexes containing soy protein hydrolysate and lecithin or modified lecithin, have also strong yellowish or brown colour and their use in light coloured products, such as some dairy products, may thus cause off-colours to the product.

The present invention by combining plant sterols and protein hydrolysates, optionally with emulsifiers and/or fat and/or mineral salt, in lipid profile improving products, such as foods, provides a way of obtaining at least similar lipid profile improving effect, especially cholesterol lowering effect, as can be obtained with protein hydrolysates alone, but with lower protein hydrolysate content and thus with less adverse effect on the taste of the food products. Complexing protein hydrolysates either with synthetic emulsifiers or with plant sterols or advantageously with both emulsifiers and plant sterols also diminishes the unpleasant taste of protein hydrolysates. The compositions according to the present invention thus widen the range of food products in which the protein hydrolysates can be incorporated to include also mild-tasting ones and still achieving at least similar serum lipid profile improving effect. The compositions of the present invention also widen the range of food products in which protein hydrolysate/emulsifier complexes can be incorporated to include also light coloured products. The present invention thus also provides a method to improve the sensory properties of lipid profile improving foods containing protein hydrolysates or protein hydrolysate/emulsifier complexes.

DETAILED DESCRIPTION OF THE INVENTION

In one aspect of the present invention there is provided a composition comprising a protein hydrolysate and a plant sterol, wherein the weight ratio of the plant sterol to the protein hydrolysate is from 1:0.02 to 1:150.

The composition of the present invention can additionally comprise an emulsifier and/or a fat. Furthermore, the composition can comprise a mineral salt.

The weight ratio of the plant sterol to protein hydrolysate in the compositions is preferably from 1:0.2 to 1:30, more preferably from 1:0.4 to 1:12.5 and most preferably from 1:1 to 1:5.

As used here, the term "protein hydrolysate" includes all hydrolyzed products of proteins prepared by using a proteolytic enzyme preparation, a microorganism containing suitable proteolytic activity or acid hydrolysis or any combination thereof, and having serum lipid profile improving effect. Commercially available hydrolysates can be used or hydrolysates can be prepared. Preferred hydrolysates have a molecular weight of 300-100 000 D, more preferably 500-50 000 D, most preferably 500-30 000 D and/or they are only slightly soluble in water.

Plant, animal or microbial proteins and/or their mixtures can be used as protein sources for the hydrolysates. Proteins of vegetable origin are preferred. Most preferred are proteins of grain or legume origin. Suitable vegetable protein sources are for example soybean protein, wheat protein, especially wheat gluten, corn protein, oat protein, rye protein, rapeseed or canola protein, barley protein, rice protein, flaxseed protein, potato protein, pea protein, lupin protein, maize protein and buckwheat protein. Of animal origin, suitable examples include milk proteins, such as whey protein, and their fractions. All these proteins can be used in different commercially available purified or non-purified forms as source for the hydrolysates. Also materials containing these proteins and other major constituents, such as carbohydrates, can be used as source for the hydrolysates.

Protein hydrolysates are preferably prepared via enzymatic hydrolysis by methods and processes well known in the art, but can also be prepared using other known hydrolytic techniques, such as acid hydrolysis. For example EP 0 790 060 A1 discloses a method for preparing suitable protein hydrolysates. Typical preparation methods include treatment of the protein moiety with a proteolytic enzyme in aqueous medium, where the protein or protein containing material is dispersed in water and pH is adjusted with an acid or a base to the optimum pH range of the enzyme to be used. The enzyme is preferably added in an amount of 0.2-5%, more preferably 0.5-2% based on the substrate protein and the reaction is carrier out at optimum temperature and pH for the time needed depending on the enzyme and the degree of hydrolysis wanted. The reaction is typically terminated by heating the mixture to a temperature high enough to inactivate the enzyme. The reaction mixture can optionally be neutralized before or after the heating step by using a suitable acid, e.g. hydrochloric acid, or a base, e.g. sodium hydroxide. Preferably the fraction having serum lipid profile improving effect is then separated from the reaction mixture. In case the water insoluble or slightly water soluble fraction of the reaction mixture is desired, it can be separated e.g. by centrifugation or filtration techniques to obtain what is here referred to as a protein hydrolysate slurry. The protein hydrolysate slurry can be used as such or as washed with water and/or dried. The process used for drying is not critical, for example freeze-drying, spray drying or any other process known in the art may be used, which produces a powder either directly or through a grinding step. Dried and powdery protein hydrolysate is especially preferred as it entraps lipids efficiently. Proteolytic enzymes that can be used in the preparation of the hydrolysates of the present invention include enzymes from plant, microbial and animal origin, including also enzymes from genetically modified organisms, that at suitable reaction conditions hydrolyse proteins to hydrolysates that have a serum lipid profile improving effect. Suitable proteolytic enzymes are e.g. pepsin, trypsin, pancreatin and papain. It is also possible to use different enzymes sequentially, e.g. pepsin and trypsin or pepsin and pancreatin. Especially preferred are the enzymes or combinations of enzymes that produce protein hydrolysates that are only poorly digestible or no longer digestible in human intestine and can thus be referred also as "resistant proteins".

As used here, the term "plant sterol" refers to any sterol as defined in the following and having lipid profile improving effect. Plant sterols include both sterols and saturated sterols i.e. stanols in either their free form or as esterified e.g. with fatty acids (2-24 carbon atoms, saturated, monounsaturated or polyunsaturated, including also special fatty acids such as conjugated fatty acids, e.g. CLA, and EPA and DHA), hydroxybenzoic acids or hydroxycinnamic acids (ferrulic or coumaric acids) or other organic acids such as e.g. di-or tricarboxylic acids and/or hydroxy acids or with any combination of the said acids. In addition, the definition of plant sterols also include glycosidic sterols and their derivatives. Any combinations of the free and various esterified and glycosylated forms are also included. As used here, the term "plant sterol in esterified form" or "plant sterol ester" refers to plant sterols having at least 60%, preferably at least 85%, most preferably at least 95% of the plant sterols in esterified form.

In this specification the sterols include 4-desmethyl sterols, 4-monomethyl sterols and 4,4-dimethyl sterols (including triterpene alcohols) and the stanols include 4-desmethyl stanols, 4-monomethyl stanols and 4,4-dimethyl stanols. Typical 4-desmethyl sterols are sitosterol, c ampesterol, stigmasterol, brassicasterol, 22-dehydrobrassicasterol, Δ5-avenasterol. Typical 4,4-dimethyl sterols are cycloartenol, 24-methylenecycloartenol and cyclobranol. Typical stanols are sitostanol, campestanol and their 24-epimers, cycloartanol and saturated forms obtained by saturation of e.g. triterpene alcohols (cycloartenol, 24-methylenecycloartenol and cyclobranol). The definition "plant sterol" includes all possible natural blends or any mixtures of named sterols and/or stanols as well as any individual sterol or stanol.

The amounts of plant sterols in this specification are calculated as plant sterol equivalents i.e. as the amount of free plant sterol.

Commercially available plant sterols in their free or esterified form can be used as such. When plant sterols in their free form are used, the particle size of the plant sterols is preferably reduced to enhance the dispersability, dissolvability and solubility of the plant sterols. Particle size reduction can be done by many techniques known in the art, e.g. by different dry or wet grinding or micromilling techniques described for example in U.S. Pat. No. 6,129,944, WO 98/58554 and EP 1 142 494 A 1. Other components, such as a suitable admixture can be pulverized together with plant sterols, the choice of the other components depending on the food material, nutraceutical or pharmaceutical in which the active ingredients are to be added.

Examples of the admixture include various structure and flavor enhancers, as well as flours especially in case the active ingredients are to be added into bakery products.

Plant sterols in their free form may also be used molten, especially in compositions containing an emulsifier and/or a fat. Preferably a homogenous mixture that is easily used in the compositions of the present invention is formed from plant sterols and an emulsifier and/or a fat by heating plant sterols to their melting point, to 60-150 ° C., typically to 130-150° C., and adding the emulsifier and/or fat to the sterols, either prior to or after heating. Suitable techniques that can be utilized are described e.g, in U.S. Pat. No. 6,190,720 B1. Most preferably a blend of plant sterols and emulsifier(s) and/or fat is heated until the components are dissolved. The mixture is cooled under agitation prior to adding it into the compositions of the present invention.

Preferably the plant sterol is esterified and most preferably it is a plant sterol fatty acid ester. The fatty acid ester is technically very suitable for incorporation into a wide range of different products and is especially preferred as it has very good organoleptic properties, enabling production of the compositions of the present invention with good organoleptic properties.

Preferably the plant sterol is a stanol because its absorption is negligible and the use of stanol is therefore safer. Also the cholesterol lowering effect seems to be stronger with stanols. Most preferred are therefore the stanol fatty acid esters for use in the compositions according to the invention.

As used here, the term "emulsifier" refers to a substance promoting the formation and improving the stability of emulsions. Emulsifiers are synthetically produced, derived through chemical modification of naturally occurring materials or natural products. The characterizing feature of emulsifiers is a structure in which one portion of the molecule is polar (hydrophilic) and the other non-polar (hydro-phobic), which allows the emulsifier to align and stabilize the contact surfaces of the two immiscible phases of the emulsion. The relative size and character of the polar and non-polar portions of the molecule, among other factors, affect the type and quality of emulsions produced. HLB (hydrophilic lipophilic balance) scale is commonly used to generally describe the emulsifying properties of emulsifiers. An emulsifier with a low HLB value (up to about 6) tends to promote W/O emulsions, an emulsifier with an intermediate HLB value W/O or O/W emulsions and an emulsifier with a high HLB value (from about 8) O/W emulsions.

Preferably the emulsifier or a mixture of emulsifiers is used to produce a complex with plant sterols and/or protein hydrolysates. Typical, but non-restricting examples of suitable emulsifiers include monoglycerides, such as distilled monoglycerides, diglycerides, monoglyceride derivatives, such as acetic, lactic, succinic or citric acid esters of monoglycerides, lecithins, modified lecithins such as enzyme modified lecithin, for example lysolecithin, polyglycerol esters, polyglycerol polyricinoleate, sorbitan esters, polysorbates, propylene glycol esters, stearoyl lactylates, such as sodium stearoyl lactylate and calcium stearoyl lactylate, diacetyl tartaric acid esters, diacetyl lactic acid esters, sugar esters, and mixtures thereof. Also lipid based grain fractions having emulsifying properties can be used as emulsifiers. These include lipid fractions e.g. from oat.

Preferred emulsifiers or mixtures of emulsifiers are those having a HLB value or emulsifying properties equivalent to a HLB value above 4, more preferably above 6. Examples of preferred emulsifiers include acetic, succinic, lactic and citric acid esters of monoglycerides, lecithins, modified lecithins, polyglycerol esters, polysorbates, diacetyl tartaric acid esters, monoglycerides, stearoyl lactylates and mixtures thereof As used here, by "synthetic emulsifier" is meant emulsifiers that are synthetically produced or derived through chemical modification of naturally occurring materials.

These synthetic emulsifiers do not have strong color, unlike some naturally occurring emulsifiers, such as lecithin and enzymatically modified lecithin. The synthetic emulsifiers can thus be used as a part of protein hydrolysate/emulsifier complexes added also into light colored products. The synthetic emulsifier are also often more pure than the naturally occuring emulsifiers. Suitable, but non-limiting examples of the synthetic emulsifiers are monoglyceride derivatives, polyglycerol esters, propylene glycol esters, polysorbates, sorbitan esters, stearoyl lactulates, diacetyl tartaric acid esters, sugar esters and mixtures thereof Preferred synthetic emulsifiers or mixtures of synthetic emulsifiers are those having a HLB value or emulsifying properties equivalent to a HLB value above 4, more preferably above 6.

As used here, the term "complex" is a composition in which only a part of the emulsifier(s) and/or fat and/or plant sterols are extractable by using non-polar solvents commonly used to extract "free lipids". These non-polar solvents include e.g. petroleum ether and hexane. The rest of the emulsifier(s) and/or fats and/or plant sterols can only be extracted after hydrolysis e.g. by using methods including acid hydrolysis, such as AOAC 922.06.

As used here, by "fat" is meant edible solid fats, semi-solid fats, liquid oils and any mixtures thereof Also fat substitutes such as sugar polyesters are included. Examples of solid and semi-solid fats that are usable include tallow, lard, butter, margarine and shortenings as well as semi-solid tropical oils, such as coconut oil and palm kernel oil. Typical examples of liquid oils include canola/rapeseed oil, soybean oil, sunflower oil, olive oil, palm oil, corn oil, sesameseed oil, cottonseed oil, wheat germ oil, peanut oil and fish oils. Liquid vegetable oils are especially preferred. The fat can be naturally occurring or modified, for example hydro-genated, transesterified, contain structured triacylglycerols or an increased amount of diacylglycerols.

As used here, the term "mineral salt" includes nutritionally beneficial mineral salts having elevated K and/or Mg and/or Ca content and/or reduced Na content compared to common salt. In U.S. Pat. No. 6,136,349 this kind of mineral salt, especially when administered together with plant sterols and/or used to replace common salt in food items, is suggested to bring beneficial health effects, such as lowering elevated blood pressure. Examples of suitable mineral salt compositions include mineral salt sold by trade name Pansalt® or Cardia® salt. The mineral salt is preferably added into the protein hydrolysate, more preferably into the protein hydrolysate slurry or washed protein hydrolysate.

In the following some typical compositions of the present invention and the preparation thereof will be explained in more detail.

The composition of the present invention comprising one or more protein hydrolysates and one or more plant sterols can be used as such or as a pharmaceutical or a nutraceutical or most advantageously in food products for improving serum lipid profile in man. The protein hydrolysate(s) and plant sterol(s) may be added in any suitable way into food products, pharmaceuticals or nutra-ceuticals separately as ingredients or they may be suitably combined to form compositions or complexes before forming the composition according to the invention. Preparation of the compositions and the incorporation into food products, pharmaceuticals or nutraceuticals can be facilitated by reducing particle size of said compositions or components thereof e.g. by grinding or micromilling. Also other components such as water or mineral salt may be added. Typical but non-restricting examples of the preparation of the compositions and complexes are described in the following embodiments.

In one embodiment of the present invention the protein hydrolysate(s) and the plant sterol(s) are added into food products, phaimaceuticals or nutraceuticals separately as ingredients. The active ingredients are added into food material, pharmaceuticals or nutraceuticals by conventional processes for producing these products.

Commercially available plant sterols in their free form can be used as such, or more preferably the particle size of the plant sterols is reduced to enhance the dispersability and solubility of plant sterols as described above. Molten plant sterols in their free form can also be used. Advantageously the main part of plant sterols is in esterified form and preferably melted, if needed, before addition into food products, pharmaceuticals or nutraceuticals. Protein hydrolysates can be used in any suitable form including protein hydrolysate slurry, washed and/or dried protein hydrolysate, protein hydrolysate in an aqueous solution or protein hydrolysate with reduced particle size.

In another embodiment of the present invention the protein hydrolysate(s) and the plant sterol(s) are combined into a composition that can be used as such or added into pharmaceuticals or nutraceuticals or food products. When plant sterols in their free form are used, they are mixed with dried protein hydrolysates to form a homogenous composition or more preferably homogenized with the protein hydrolysate slurry or water washed protein hydrolysate to form a protein hydro-lysate/plant sterol complex. The mixture may be used as such or preferably be dried by methods commonly used in the art, e.g. by freeze drying or spray drying, to form powder either directly or through a grinding step. Commercially available plant sterols can be used as such or preferably with reduced particle size. In a preferred embodiment the main part of the plant sterols is in esterified form. Esterified plant sterols are preferably mixed with a dried and powdery protein hydrolysate to form a protein hydrolysate/plant sterol complex.

Instill another embodiment of the present invention the protein hydrolysate(s), mineral salt and the plant sterol(s) are combined into a composition that can be used as such or added into pharmaceuticals or nutraceuticals or food products. The mineral salt is preferably added into the protein hydrolysate, more preferably into the protein hydrolysate slurry or washed protein hydrolysate and the mixture is combined with plant sterols.

Alternatively the compositions comprising the protein hydrolysate(s) and the plant sterol(s) can be prepared by exposing a mixture of unhydrolyzed protein(s) and plant sterol(s) to hydrolysis, preferably to enzymatic hydrolysis by methods and processes known in the art.

The composition of the present invention comprising one or more protein hydro-lysates, one or more emulsifiers and/or fats and one or more plant sterols can be used as such or as pharmaceuticals or nutraceuticals or most advantageously in food products for improving serum lipid profile in man. The protein hydrolysate(s), plant sterol(s) and emulsifier(s) and/or fat(s) may be added in any suitable way into food products, pharmaceuticals or nutraceuticals separately as ingredients or they may be suitably combined to form compositions or complexes before forming the composition according to the invention, which is incorporated in the food products, pharmaceuticals or nutraceuticals. Preparation of the compositions and the incorporation into food products, pharmaceuticals or nutraceuticals can be facilitated by reducing particle size of said compositions or components thereof e.g. by grinding or micromilling. Also other components such as water or mineral salt may be added. Typical but non-restricting examples of the preparation of the compositions and complexes are described in the following embodiments. Preferably the emulsifier is used to produce a complex with protein hydrolysate(s) and/or plant sterol(s).

In one embodiment of the present invention the protein hydrolysate(s) and the emulsifier(s) are used to form a protein hydrolysate/emulsifier complex, and the complex and the plant sterols are added into food products, pharmaceuticals or nutraceuticals separately as ingredients. The active ingredients are added into food material, pharmaceuticals or nutraceuticals by conventional processes for producing these products.

The protein hydrolysate/emulsifier complex can be prepared by mixing the emulsifier and protein hydrolysate e.g. by a high speed mixer, or more preferably by forming a protein hydrolysate/emulsifier complex by mixing the ingredients in the presence of water. Preferably the emulsifier is dispersed in water, protein hydro-lysate added, followed by thorough mixing at room temperature. Optionally the complex is dried by conventional drying techniques, such as e.g. freeze-drying or spray-drying, to form a powdery product either directly or through a grinding step. The complex can also be prepared of the protein hydrolysate and a mixture of emulsifier and fat, with or without the presence of water. The protein hydrolysate/emulsifier complex contains preferably at least 5%, more preferably at least 10%, and most preferably at least 20% emulsifier on dry weight basis Also any commercially available protein hydrolysate/phospholipid complex can be used as protein hydrolysate/emulsifier complex.

Prior art discloses protein/phospholipid and protein hydrolysate/phospholipid complexes containing 10% or more bound phospholipid (EP 0 790 060 A1), especially lecithin or enzyme modified lecithin, where both the protein or protein hydrolysate and phospholipids have lipid metabolism improving effect. In the present invention a wider range of emulsifiers or their combinations can be used. This is of particular benefit when the complex is added into food products, pharmaceuticals or nutraceuticals, where the emulsifiers can be selected to bring advantageous effects on the properties, e.g. texture or taste, of the final product and not just solely on the basis of enhancing the lipid profile improving effect of the protein hydrolysate.

Commercially available plant sterols in their free form can be used as such, or more preferably the particle size of the plant sterols is reduced to enhance the dispersability and solubility of plant sterols. Particle size reduction can be done by many techniques known in the art, e.g. by grinding. Advantageously the main part of plant sterols is in esterified form and preferably melted, if needed, before addition into food products, pharmaceuticals or nutraceuticals.

In another embodiment of the present invention plant sterols in a form of a plant sterol/emulsifier complex, or plant sterols dissolved or suspended in a fat, and protein hydrolysate are added into food products, pharmaceuticals or nutraceuticals separately as ingredients. The active ingredients are added into food material, pharmaceuticals or nutraceuticals by conventional processes for producing these products. The plant sterol/emulsifier complex or the suspension or solution containing plant sterols and fat is prepared by dissolving or suspending plant sterols in their free form, preferably with reduced particle size, in a melt of an emulsifier, a fat or a mixture of emulsifier and fat at elevated temperatures, preferably at >60° C., more preferably at >80° C., mixing to form a homogenous dispersion or solution and cooling with agitation. Also molten plant sterols may be used. The weight ratio of plant sterols to emulsifier can be from 1:0.01 to 1:5, preferably from 1:0.05 to 1:2, more preferably from 1:0.1 to 1:2. The crude fat content, excluding plant sterols and emulsifiers, is preferably less than 80%, more preferably less than 60%, most preferably less than 20% of the weight of the complex or dispersion or solution. Also plant sterols mainly in their esterified form may be used instead of plant sterols in their free form. Protein hydrolysates can be used in any suitable form including protein hydrolysate slurry, washed and/or dried protein hydrolysate, protein hydrolysate in an aqueous solution, protein hydrolysate with reduced particle size and protein hydrolysate/emulsifier complex.

In a preferred embodiment of the present invention the plant sterol(s), the emulsifier(s) and the protein hydrolysate(s) are combined into a protein hydro-lysate/plant sterol/emulsifier complex that can be used as such or added into pharmaceuticals or nutraceuticals or food products.

The complex is preferably prepared by first dissolving or suspending plant sterols in a melt of an emulsifier, a fat or a mixture of emulsifier and fat at elevated temperatures, preferably at >60° C., more preferably at >80° C., mixed to form a homogenous dispersion or solution and cooled with agitation. The weight ratio of plant sterols to emulsifier can be from 1:0.01 to 1:5, preferably from 1:0.05 to 1:2, more preferably from 1:0.1 to 1:2. The fat content, excluding plant sterols and emulsifiers, is preferably 0-80%, more preferably 0-60%, most preferably 0-20% of the weight of the complex or suspension or solution. Protein hydrolysate in a dry form, as a slurry or a water washed protein hydrolysate or an aqueous protein hydrolysate suspension or solution is then mixed and homogenized with the cooled plant sterol/emulsifier or plant sterol/fat or plant sterol/emulsifier/fat mixture to form a protein hydrolysate/plant sterol/emulsifier complex or if no emulsifier is present, a protein hydrolysate/plant sterol complex. The homogenized mixture can optionally be dried and/or its particle size reduced before usage. Plant sterols in their free form are preferably used. Plant sterols in their free form with reduced particle size are especially preferred. Also molten plant sterols may be used. Plant sterols mainly in their esterified form may also be used. The complex may also be prepared by combining a protein hydrolysate/emulsifier complex and plant sterols.

Alternatively the compositions consisting the protein hydrolysate(s), the emulsifier(s) and/or fat(s) and the plant sterol(s) can be prepared by first exposing a complex of unhydrolyzed protein/emulsifier or unhydrolyzed protein/plant sterols or unhydrolyzed protein/plant sterols/emulsifier(s) to hydrolysis, preferably to enzymatic hydrolysis by methods and processes known in the art and described earlier, and then combining the hydrolyzed complex with other components according to the present invention.

In a second aspect of the present invention there is provided a composition comprising a protein hydrolysate and emulsifier(s) or emulsifier-fat mixture for improving serum lipid profile in man, wherein the synthetic emulsifier(s) are used. By using synthetic emulsifiers, the taste, colour and impurity problems commonly attributed to compositions containing natural emulsifiers can be avoided. Also the lipid based grain fraction(s) having emulsifying properties can be used as emulsifiers in a composition comprising a protein hydrolysate and emulsifier(s) or emulsifier-fat mixture. In this third aspect of the invention the protein hydrolysate and the emulsifier are perferably obtained from the same source. E.g. oat is fractionated and a protein rich fraction is hydrolysed and combined with a lipid rich fraction to a mixture or a complex. A benefit with this combination is that it is made of non-allergenic materials.

The composition of the present invention comprising one or more protein hydro-lysates and one or more synthetic emulsifiers and optionally fat(s), and/or one or more lipid based grain fractions having emulsifying properties, can be used as such or as pharmaceuticals or nutraceuticals or most advantageously in food products for improving serum lipid profile in man. The protein hydrolysate(s) and synthetic emulsifier(s), and optionally fat(s), or the protein hydrolysate(s) and lipid based grain fractions having emulsifying properties may be added in any suitable way into food products, pharmaceuticals or nutraceuticals separately as ingredients or they may be suitably combined to form compositions or complexes before forming the composition according to the invention, which is incorporated in the food products, pharmaceuticals or nutraceuticals. Preferably the synthetic emulsifier or lipid based grain fraction is used to produce a complex with protein hydrolysate(s) by methods described earlier.

In a further aspect of the present invention there is provided a food product comprising at least one basic nutritional ingredient and at least one of the compositions of the present invention as defined above.

The plant sterol constituent of the composition is present in a higher amount than naturally occurring in the basic nutritional ingredient(s).

The food product of the present invention can be prepared by adding said composition to food material(s) by the conventional processes for producing food products. The composition can be added as such (either in liquid, semi-solid or dried form) or the constituents of the composition can be added separately as ingredients.

The food product of the present invention can be in the form of various food compositions, including but not restricted to bakery products and confectionery (fresh and dry bakery products, e.g. fresh bread, other bread products, cakes, muffins, waffles, biscuits, crackers, protein enriched bakery products etc.)

cereal products and snacks (breakfast cereals, muesli, bars, such as cereal based and muesli bars, such bars possibly containing chocolate, pasta products, flours etc.)

beverages (alcoholic and non-alcoholic drinks, including e.g. soft drinks, juices and juice-type mixed drinks, fortified beverages such as e.g. protein or calcium fortified beverages, probiotic drinks, sports and energy drinks, dietary supplement and meal replacement drinks, concentrates or premixes for beverages and powdered drinks where the content of compositions of the present invention is calculated for the ready-to-use form, etc.)

dairy products (milk, milk based products, e.g. cheese, cream cheese and the like, yogurt, frozen yogurt, other frozen dairy foods, drinkable yogurt, other fermented milk products, dairy beverages, ice cream, desserts, spreads etc.)

fermented cereal products sauces, soups meat, fish, poultry and egg products (e.g. sausages, meat balls etc.)

analogues for e.g. dairy or meat products (e.g. imitations of cheese, yogurt, ice cream, desserts, meat substitutes, milk alternatives etc.), non-dairy frozen desserts soy based products vegetable oil based products (e.g. margarines, spreads, dressings, mayonnaise etc.)

ready mixes (for baking e.g. breads, cakes, muffins, waffles, pizzas, pancakes; or for cooking e.g. soups, sauces, desserts, puddings) to be used in preparing or manufacturing foods.

The food product of the present invention can also contain other nutritionally beneficial components, some of which may further enhance the effects of the compositions of the present invention. The food can be fortified with these components or the components can be an intrinsic part of the other food ingredients.

Examples of the nutritionally beneficial components include diacylglycerol and n-3 fatty acids, e.g. from fish oil, which have advantageous effects on the lipid metabolism and may thus reduce the risk of cardiovascular disease. N-3 fatty acids act favourably on blood characteristics, e.g. they are hypotriglyceridemic and reduce platelet aggregation. Diacylglycerol reduces serum triacylglycerol levels and can thus have a favourable effect on the risk of cardiovascular disease. Both n-3 fatty acids and diacylglycerols may lower risk of atherosclerosis and CVD mortality also by other mechanisms.

Other non-limiting examples of the beneficial nutritional components include dietary fibre and beneficial minor components, for example such as isoflavones, tocopherols, tocotrienols, carotenoids, vitamin C, folate and flavonoids. Also other vitamins and minerals may be added or included in the food products of the present invention.

Especially the use of dietary fibre may further enhance the effects of the present compositions. By dietary fibre, it is meant food components derived from plant material, or analogous carbohydrates from other sources, that are resistant to digestion and absorption by human digestive enzymes. This includes various polysaccharides, oligosaccharides, lignins and associated substances that are resistant to digestion. Dietary fibre may further be classified into water-soluble and water insoluble fractions. Examples of the water-soluble fraction are e.g. pectin, plant gums, β-glucans and resistant starch and of the insoluble fraction e.g. cellulose and hemicellulose. An adequate fibre intake is thought to have many beneficial effects, for example viscous soluble fibre is known to reduce risk of cardiovascular disease by lowering plasma cholesterol levels. In a further aspect of the present invention there is provided a pharmaceutical or nutraceutical product for improving serum lipid profile comprising a composition of the present invention as defined above. Said product can additionally contain at least one compounding agent. The compounding agent can be any pharmaceutically acceptable binder, carrier, diluent, excipient or coating agent. The product can be in any suitable form, e.g. tablets, granules, powder, capsules, syrups, dispersions or other liquid preparations for oral administration.

The products and compositions of the present invention preferably contain at least two active ingredients, i.e. protein hydrolysate(s) and plant sterol(s), in sufficient amounts to provide improvement in serum lipid profile, e.g. reduction in serum total and/or LDL cholesterol levels. The invention is especially directed to synergistic combination of at least two active ingredients, i.e. protein hydrolysate(s) and plant sterol(s), the use of which leads to enhanced improvements in serum lipid profile compared to the effects obtained when one of the ingredients is used alone. Certain protein hydrolysate/plant sterol/emulsifier complexes according to the present invention are especially beneficial as the lipid profile improving effect is optimized by ensuring optimal availability of the active ingredients at the critical sites of action. In addition to reduction of serum total and LDL cholesterol levels, some compositions of the present invention also provide desired increase in serum HDL cholesterol levels. Some of the compositions also have a beneficial effect on blood pressure. The invention is also directed to combinations of active ingredient(s) and ingredient(s) ensuring the optimal availability of the active ingredient at the site of action, i.e. protein hydrolysate(s) and synthetic emulsifier(s).

The present invention also makes it possible to reduce the daily intake of plant sterols in man and still achieving similar cholesterol lowering effects as obtained with the generally recommended daily intake of plant sterols (2-3 g) which can be achieved e.g. by consuming commercial products enriched with plant sterols. The optimal daily intake of the compositions of the present invention as such or when used in foods, nutraceuticals or pharmaceuticals is such that a daily intake of plant sterols (calculated as sterol equivalents) of 0.4-5 g, preferably 0.5-2.5 g, more preferably 0.8-2 g is supplied.

According to the present invention it is also possible to lower the protein hydro-lysate content of food products containing protein hydrolysates especially purposed for improving serum lipid profile, thus improving the organoleptic properties of such foods. The optimal daily intake of the compositions of the present invention as such or when used in foods, nutraceuticals or pharmaceuticals is such that a daily intake of protein hydrolysate of 0.1-60 g, preferably 0.5-15 g, more preferably 0.8-10 g is supplied.

The invention is also directed to food products containing at least 10% of the optimal daily intake of the plant sterols and protein hydrolysates per serving. Preferably the food products contain from 10% to 200% of the optimal daily intake of plant sterols and protein hydrolysates per serving.

Typically the plant sterol content of the food products is between 0.05-20 g per 100 g food product, preferably 0.1-15 g/100 g, more preferably 0.1-10 g/100 g, and most preferably 0.5-5 g/100 g and the protein hydrolysate content is between 0.0002-20 g per 100 g food product, preferably 0.0005-15 g/100 g, more preferably 0.001-10 g/100 g, and most preferably 0.1-10 g/100 g.

In yet a further aspect of the present invention there is provided a method for improving serum lipid profile e.g. for lowering total and/or LDL cholesterol, increasing HDL cholesterol, reducing triacylglycerol, reducing apolipoprotein B and/or increasing the ratio of HDL cholesterol to LDL cholesterol in a subject, comprising orally administering to the subject a composition according to the present invention in an amount effective for improving serum lipid profile.

Further, the present invention provides a method to reduce or prevent the development of atherosclerosis in humans by dietary means including orally administering to the subject a composition according to the present invention in an amount effective for improving serum lipid profile.

The main advantages of the present invention obtained by combining the intake of the two active ingredients are:
- synergistic serum lipid profile improving effect of plant sterols and protein hydrolysates
- enhanced serum lipid profile improving effect compared to what is achievable by using plant sterols or protein hydrolysates alone
- lower daily intake of plant sterols is needed to achieve the same serum lipid profile improving effect than what is achieved by using plant sterols alone
- lower daily intake of protein hydrolysates is needed to achieve the same serum lipid profile improving effect than what is achieved by using protein hydro-lysates alone
- lowering the risk of cardiovascular disease by means of improving serum lipid profile.

The present invention is especially directed to enhanced serum lipid profile improving effect by utilizing the synergistic combination of plant sterols and protein hydrolysates, optionally with emulsifiers and/or fat and/or mineral salt. The present invention is also directed to ensuring optimal availability of the active ingredients, especially protein hydrolysates, at the site of action. Certain compositions containing protein hydrolysates and emulsifiers or protein hydrolysates, emulsifiers and plant sterols according to the current invention are especially beneficial as the lipid profile improving effect is optimized by ensuring optimal availability of the active ingredients.

The present invention is also especially directed to an optimized daily intake of plant sterol and protein hydrolysate to achieve a significant serum lipid profile improving effect in a form of a food product as part of the daily diet. The daily intake of plant sterols can be decreased by combining the beneficial effect of plant sterols and other lipid profile improving dietary components to achieve similar lipid profile improving effect as obtained with currently recommended daily intake (2-3 g/d) of plant sterols. This approach advantageously reduces the daily intake of plant sterols, leading to a more balanced use of plant sterols. The synergistic effect is especially profound at daily intakes of at most 2 g plant sterol.

In a preferred embodiment of the invention the compositions contain plant sterols and soy protein hydrolysate, optionally with emulsifier(s). Preferably the plant sterol used is a plant sterol fatty acid ester and even more preferred it is a plant sterol fatty acid ester containing a substantial amount of stanol fatty acid ester, preferably at least 30% stanol fatty acid ester.

The compositions according to the present invention are most preferably incorporated into foods designed for being a part of a healthy diet.

Additional aspects of the invention are:
Use of a composition according to any one of claims 1 to 13 for the preparation of a pharmaceutical, nutraceutical or food product for improving serum lipid profile, especially for lowering serum total and/or LDL cholesterol and/or for increasing the ratio of HDL cholesterol to LDL cholesterol and/or for lowering the serum apolipoprotein B level.

Use of a composition according to any one of claims 1 to 13 for the preparation of a pharmaceutical, nutraceutical or food product for reducing or preventing the development of atherosclerosis.

The above uses wherein the protein hydrolysate is administrated at a rate of 0.1 to 60 g, preferably 0.5 to 15 g and more preferably 0.8 to 10 g per day, and the plant sterol is administrated at a rate of 0.4 to 5 g, preferably 0.5 to 2.5 g and more preferably 0.8 to 2 g per day calculated as sterol equivalents.

A method for improving serum lipid profile, especially for lowering serum total and/or LDL cholesterol and/or for increasing the ratio of HDL cholesterol to LDL cholesterol and/or for lowering the serum apolipoprotein B level in a subject, comprising orally administering to the subject a composition according to any one of claims 1 to 13, in an amount effective for improving serum lipid profile.

A method for reducing or preventing the development of atherosclerosis in a subject by dietary means including orally administering to the subject a composition according to any one of claims 1 to 13, in an amount effective for improving serum lipid profile.

The above methods wherein the protein hydrolysate is administrated at a rate of 0.1 to 60 g, preferably 0.5 to 15 g and more preferably 0.8 to 10 g per day, and the plant sterol is administrated at a rate of 0.4 to 5 g, preferably 0.5 to 2.5 g and more preferably 0.8 to 2 g per day calculated as sterol equivalents.

The invention is further illustrated by the following examples. Examples 1-4 illustrate preparation of the constituents of the compositions, examples 5-8 illustrate preparation of the compositions according to the invention, examples 9-16 illustrate the use of the compositions in food products and example 17 illustrates the effect of a composition of the present invention in lowering serum cholesterol. In this specification the percentages mean % by weight unless otherwise specified.

EXAMPLE 1

Preparation of protein hydrolysate.

1500 g isolated soy protein (SUPRO® Brand Isolated Soy Protein, Protein Technologies International) was dispersed in 15 l of water, pH was adjusted to 2 with HC1, and pepsin (P7000, Sigma Aldrich, activity 1:10,000) was added to the solution (1% of the amount of isolated soy protein). The reaction was carried out at 37° C., for 24 hours and stopped by heating the reaction mixture to 85° C. for one hour. The mixture was neutralized with sodium hydroxide (2 moUl) and centrifuged. The precipitate was washed twice with water after which the protein hydrolysate was freeze-dried and ground. 300 g dried protein hydrolysate was obtained. The molecular weight of the peptides obtained in the hydrolysis was determined by SDS-polyacrylamide gel electrophoresis (SDS-page) method. The molecular weight range of the peptides in the hydrolysate was from 3000 to 30000 D.

EXAMPLE 2

Preparation of protein hydrolysate/emulsifier complex.

62 g of emulsifier (lysolecithin, Precept 8160, Central Soya) was dispersed in water (2500 ml) in room temperature and 500 g soy protein hydrolysate prepared as in example 1 was added. The solution was mixed by a high speed mixer (10 000 rpm), the mixture was freeze-dried and ground to obtain protein hydrolysate/emulsifier complex.

The total lipid content of the complex was determined by an acid hydrolysis method (AOAC 922.06). The lipids that were not bound or only loosely bound to the complex were determined by direct petroleum ether extraction (free lipids). The content of bound lipids was calculated as the difference of total and "free" lipids. Total lipid content was 11.0% of the complex, free lipid content 7.9% of the complex and thus the "bound" lipid content was 3.1% of the complex.

EXAMPLE 3

Preparation of plant sterol/emulsifier complex using plant sterols in their free form.

Plant sterol/emulsifier complex was prepared of plant sterols in their free form (Phytosterols, Archer Daniels Midland Company), sodium stearoyl lactylate (Grindsted SSL P 55, Danisco Cultor) and citric acid ester of monoglycerides (Grindsted™ Citrem P 70, Danisco Cultor). Sodium stearoyl lactylate (30 g, beads) and citric acid esters of monoglycerides (70 g, paste) were melted at 60° C. and mixed homogenous. Plant sterols (100 g) were added into the emulsifier mixture, the ingredients were mixed together and heated under agitation to about 145° C. Clear liquid obtained was then cooled with stirring to 70° C. and used for preparation of a salad dressing (in the example 11).

EXAMPLE 4

Preparation of plant sterol/emulsifier complex using plant sterols both in their free and esterified forms.

Plant sterol/emulsifier complex was prepared of a mixture of plant sterols in their free and esterified forms and lecithin. Plant sterol ester (150 g, Sterol ester-115, Raisio Benecol) was molten at 80° C. Plant sterols (100 g, Phytosterols, Archer Daniels Midland Company), with reduced particle size, and lecithin (100 g, Adlec, Archer Daniels Midland Company) were mixed into molten sterol ester and the mixture was heated under agitation to melt the crystalline plant sterols. The product was homogenized with a high speed mixer (25 000 rpm) and cooled with stirring to 60° C.

EXAMPLE 5

Preparation of protein hydrolysate/emulsifier complex by using a synthetic emulsifier.

35 g of emulsifier (citric acid ester of monoglycerides, Grindsted™ Citrem P 70, Danisco Cultor) was dispersed in water (1500 ml) at 50° C. and 150 g of the soy protein hydrolysate prepared in example 1 was added. The solution was mixed by a high speed mixer (25 000 rpm), the mixture was freeze-dried and ground to obtain protein hydrolysate/ emulsifier complex.

EXAMPLE 6

Preparation of protein hydrolysate/plant sterol complex using plant sterols in their free form.

Isolated soy protein (500 g, SUPRO® Brand Isolated Soy Protein, Protein Technologies International) was hydrolyzed as in example 1 and washed twice with water after hydrolyzation. Plant sterols in their free form (40 g, Phytosterols, Archer Daniels Midland Company) were added and homogenized with the washed protein hydrolysate with a high speed mixer (25 000 rpm). The composition was freeze-dried and ground.

EXAMPLE 7

Preparation of protein hydrolysate/plant sterol complex containing mineral salt, using plant sterols in their esterified form.

Isolated soy protein (500 g, SUPRO® Brand Isolated Soy Protein, Protein Technologies International) was hydrolyzed as in example 1 and washed twice with water after hydrolyzation. Mineral salt (5 g, Pansalt®) was added to the washed hydrolysate slurry and the slurry was freeze-dried and ground. 34.4 g plant sterol ester (Sterol ester-115, Raisio Benecol) was added to 65.6 g of the dried hydro-lysate. The mixture was homogenized with a high speed mixer (25 000 rpm).

EXAMPLE 8

Preparation of protein hydrolysate/plant sterol/emulsifier complex.

Soy protein hydrolysate was prepared as in example 1. Enzyme modified lecithin (20 g, Precept 8160, Central Soy Company) and citric acid esters of monoglycerides (50 g Grindsted™ Citrem P 70, Danisco Cultor) were melted at 60° C. and mixed homogenous. Plant sterols (50 g, Phytosterols, Archer Daniels Midland Company) with reduced particle size were added into the emulsifier mixture, the ingredients were mixed together and heated under agitation to 100° C. Clear liquid obtained was then cooled with stirring until the temperature reached 90° C. Dried and ground soy protein hydrolysate (90 g) was added and homogenized into the plant sterol emulsifier blend at 90° C. The mixture was cooled to 70 ° C. and used for preparation of a milk alternative (in the example 15) and a fruit drink (in the example 16).

The weight ratio of plant sterol to protein hydrolysate in the complex was 1:1.8 and the complex contained 23.8% plant sterols and 42.9% soy protein hydrolysate.

EXAMPLE 9

Food bar with protein hydrolysate/plant sterol complex.
Food bar was prepared of the following ingredients:

| | |
|---|---|
| 300 g | oat flakes |
| 95 g | fiber rich oat bran |
| 140 g | corn syrup |
| 50 g | brown sugar |
| 40 g | concentrated apple juice |
| 20 g | apple |
| 30 g | raisin |
| 100 g | vegetable fat |
| 3 g | salt |
| 8 g | flavoring |
| 110 g | complex from example 6 |
| 4 g | lecithin |
| A 45 g | food bar contained 1.6 g plant sterols and 3.9 g soy protein hydrolysate. |

EXAMPLE 10

Yogurt with protein hydrolysate/emulsifier complex and plant sterols.

Plant stanol ester (STAEST-115, Raisio Benecol) and protein hydrolysate/-emulsifier complex from example 5 were used separately as ingredients in preparation of yogurt. Plant stanol ester (STAEST-115) was molten at 70° C. Molten stanol ester (110 g) and 140 g soy protein hydrolysate/emulsifier complex from example 5 were added into 5,75 l of skimmed milk at 70° C., mixed with a high speed mixer and the mixture was pasteurized. Normal yogurt cultures and *Bifidobacteria* were stirred into the mixture and the mixture was held at 42° C. for 7 hours.

A 150 g serving of the product contained 1.7 g plant stanols and 3.0 g protein hydrolysate.

EXAMPLE 11

Low-fat salad dressing with plant sterol/emulsifier complex and protein hydro-lysate.

Plant sterol complex from example 3 and soy protein hydrolysate from example 1 were used separately as ingredients in a preparation of low-fat salad dressing.

Ingredients of the salad dressing were:

| | |
|---|---|
| 7.5 g | plant sterol/emulsifier complex from example 3 |
| 7 g | soy protein hydrolysate from example 1 |
| 16 g | soybean oil |
| 56 g | water |
| 6 g | vinegar |
| 4.5 g | sugar |
| 1.5 g | salt |
| 0.1 g | xanthan gum |
| 0.4 g | lemon juice |
| 1 g | spices |
| 30 g | serving of the salad dressing contained 1.1 g plant sterols and 2.1 g soy protein hydrolysate. |

EXAMPLE 12

Yogurt-like cereal product with plant sterol/emulsifier complex and protein hydrolysate.

Protein hydrolysate was prepared from wheat gluten (Raisio) in a similar way as soy protein hydrolysate in example 1, except the hydrolysate was not dried. Water was added into the washed gluten hydrolysate to obtain a product having a solid content of 20%.

Plant sterol/emulsifier complex from example 4 and wheat gluten hydrolysate were used in a preparation of fermented, yogurt-like cereal product.

Ingredients

| | |
|---|---|
| 45% | water |
| 16.5% | prepared mixture of gluten hydrolysate and water |
| 8.9% | oat bran |
| 28% | berry jam (containing fructose, blueberry, strawberry, raspberry. pectin, flavors) |
| 1.6% | plant sterol/emulsifier complex from example 4 |

The mixture of water and oat bran was fermented using Bifidobacteria culture. The berry jam, sterol/emulsifier complex and mixture of gluten hydrolysate and water were added and all ingredients worked together.

A 150 g serving of the product contained 1.3 g plant sterols and 5.0 g protein hydrolysate.

EXAMPLE 13

Bread rolls with protein hydrolysate/plant sterol complex containing mineral salt.

Bread rolls containing the complex from example 7 were prepared in a conventional way of the following ingredients:

| | |
|---|---|
| 800 g | wheat flour |
| 20 g | sugar |
| 20 g | salt |
| 10 g | margarine (80% fat content) |
| 94 g | complex from example 7 |
| 500 g | water |
| 11 g | dried yeast |
| 24 | bread rolls were obtained from the dough. Two 50 g bread rolls contained suitable daily doses of plant sterols (1.3 g) and protein hydrolysate (4.0 g). |

EXAMPLE 14

Cream cheese style spread with plant sterols and protein hydrolysate with mineral salt.

Plant stanol ester (STAEST-1 15, Raisio Benecol) and soy protein hydrolysate with mineral salt were used separately as ingredients in a preparation of cream cheese style spread. Soy protein hydrolysate containing mineral salt was prepared in a similar way as the complex in example 7, except no plant sterol ester was added into the dried and ground protein hydrolysate. The dried soy protein hydrolysate contained 4.8% mineral salt.

Plant stanol ester was first incorporated into a fat blend, composition of which was 59.7% rapeseed oil, 7% interest-erified blend of palm stearine and coconut oil and 33.3% plant stanol ester (STAEST-1 15, Raisio Benecol). The blend was prepared by blending the melted stanol ester with rapeseed oil and the hardstock component.

The cream cheese style spread was produced according to the following recipe:

| | |
|---|---|
| 51.3% | curd |
| 24.6% | fat blend including the stanol ester |
| 12.0% | condensate |
| 1.0% | stabilizer |
| 1.0% | milk proteins |
| 7.9% | soy protein hydrolysate containing 4.8% mineral salt |
| 0.3% | salt |
| 0.1% | potassium sorbate |
| 1.7% | garlic flavor preparation |
| 0.05% | lactic acid as pH-regulating agent |
| | flavors |

A serving of 20 g of the cream cheese style spread contained 1 g plant sterols (as plant stanols) and 1.5 g protein hydrolysate (as soy protein hydrolysate).

EXAMPLE 15

Milk alternative with protein hydrolysate/plant sterol/emulsifier complex. Protein hydrolysate/plant sterol/emulsifier complex from example 8 was used in production of vanilla flavored milk alternative.

Ingredients

| | |
|---|---|
| 5 l | soymilk (2% fat) |
| 94.5 g | complex from example 8 |
| | vanilla flavoring |

The soy protein hydrolysate/plant sterol/emulsifier complex from example 8 was added under vigorous stirring to soymilk having a temperature of 70° C. and homogenized. 2 dl serving of the soymilk contained 0.9 g of plant sterols and 1.6 g of soy protein hydrolysate.

EXAMPLE 16

Fruit drink with protein hydrolysate/plant sterol/emulsifier complex.

The protein hydrolysate/plant sterol/emulsifier complex from example 8 was used in preparation of fruit drink of the following ingredients:

| | |
|---|---|
| 200 g | fruit juice concentrate (orange, pineapple, passion fruit, guava, mango) |
| 776 g | water |
| 8.5 g | fructose |
| 1.5 g | calcium lactate |
| 14 g | complex from example 8 |

The fruit juice concentrate, water, fructose and calcium lactate were mixed together and heated to 70° C. The soy protein hydrolysate/plant sterol/emulsifier complex from example 8 was added under vigorous stirring to the drink and homogenized.

Two glasses (a 2 dl) of the drink contained 1.3 g of plant sterols and 2.4 g of protein hydrolysate.

EXAMPLE 17

Lipid profile improvement obtained by using a composition of the present invention.

The lipid profile improving effect of a composition containing plant sterols (as plant stanol fatty acid ester) and protein hydrolysate/emulsifier complex (as soy protein hydrolysate/lysolecithin complex from example 2) was studied by using LDL-receptor deficient female mice as test animals.

The aim of the test was to study the serum total cholesterol and triglyceride lowering effect that could be obtained by using only a small amount of plant sterols (0.5%, as sterol equivalents) as part of a atherogenic diet containing protein hydrolysate. The protein hydrolysate was administered in an amount to yield the maximum cholesterol lowering effect that could be obtained by using the hydrolysate in this animal model and still not compromising the nutritional needs and growth of the mice. The suitable amount of the hydrolysate was found to be ½ (as N equivalents) of the total protein content of the diet.

The animals were assigned into 4 groups (n=8-10 in each group) and fed experimental diets for 8 weeks.

All the experimental diets were formulated to contain 20% protein. In the control group and in the test group 2, the sole protein source was casein (88% purity). In the test groups 3 and 4, the protein source was half casein and half (as N equivalents) the protein hydrolysate/emulsifier complex. Test groups 2 and 4 contained 0.84% plant stanol fatty acid ester (0.5% as sterol equivalents). Control group and test group 3 contained 0.35% rapeseed oil to bring the equal amount of calories and equal fatty acid composition, compared to the test groups getting plant stanol ester.

Experimetal diets and results:

| | Group 1 (control) % of total | Group 2 (plant stanol ester) % of total | Group 3 (protein hydrolysate/ emulsifier complex) % of total | Group 4 (plant stanol ester + protein hydrolysate/ emulsifier complex) % of total |
|---|---|---|---|---|
| Ingredients | | | | |
| Diet premix * | 58.72 | 58.22 | 55.44 | 54.95 |
| Cocoa butter | 17.96 | 17.96 | 17.97 | 17.97 |
| Rapeseed oil | 0.35 | 0.00 | 0.35 | 0.00 |
| Plant stanol ester | 0.00 | 0.84 | 0.00 | 0.84 |
| Casein powder | 22.72 | 22.73 | 11.36 | 11.37 |
| Soy protein hydrolysate/ lysolecithin complex, from example 2 | 0.00 | 0.00 | 14.62 | 14.62 |
| Cholesterol | 0.250 | 0.250 | 0.250 | 0.250 |
| Results | | | | |
| Serum total cholesterol (mmol/l), mean | 20.6 | 14.7 | 15.5 | 11.4 |
| Change (%) compared to control group | — | −28.5 | −25.0 | −44.5 |
| Serum triglycerides (mmol/l), mean | 2.2 | 2.4 | 1.9 | 1.3 |
| Change (%) compared to control group | | +8.8 | −10.9 | −39.1 |

* Clinton/Cybulsky (D12106px, without protein), from Research Diets Inc.

As shown in the table, both plant stanol ester and protein hydrolysate/emulsifier complex had serum cholesterol lowering effect (groups 2 and 3, respectively). A composition of the present invention (group 4), the combination of plant sterols and protein hydrolysate/emulsifier complex, had even enhanced cholesterol lowering effect compared to the plant sterols (group 2) or protein hydrolysate/emulsifier complex (group 3) alone and compared to what was expected for the combination. Thus even when the maximal amount of protein hydrolysate was used in the feed addition of plant sterols effectively further reduced serum total cholesterol levels Protein hydrolysate/emulsifier complex (group 3) had serum triglyceride reducing effect, whereas the serum triglyceride level was somewhat raised in the group 2 receiving plant sterols. Surprisingly, the combination of plant sterols and protein hydrolysate/emulsifier complex had a strong synergistic triglyceride lowering effect.

By combining plant sterols and protein hydrolysate, according to the present invention, remarkable synergistic lipid profile improvements could be seen.

We claim:

1. A method of lowering serum triglycerides in a subject in need thereof, comprising administering to the subject an oral therapeutical composition comprising a soybean protein hydrolysate and a plant sterol, wherein the weight ratio of the plant sterol to the soybean protein hydrolysate is from 1:0.02 to 1:150.

2. The method according to claim 1, wherein the composition comprises an additional component selected from the group consisting of emulsifiers, fats, mineral salts and mixtures thereof.

3. The method according to claim 1, wherein the plant sterol is selected from the group consisting of free sterols, free stanols, sterols in esterified form, stanols in esterified form and mixtures thereof.

4. The method according to claim 2, wherein the emulsifier is selected from the group consisting of monoglycerides, diglycerides, lecithins, modified lecithins, polyglycerol esters, polyglycerol polyricinoleate, sorbitan esters, polysorbates, propylene glycol esters, stearoyl lactylates, diacetyl tartaric acid esters, diacetyl lactic acid esters, sucrose esters, monoglyceride derivatives selected from the group consisting of acetic, lactic, succinic and citric acid esters of monoglycerides, and mixtures thereof.

5. The method according to claim 2, wherein the emulsifier has a hydrophilic lipophilic balance (HLB) of at least 4.

6. The method according to claim 1, wherein the weight ratio of the plant sterol to the soybean protein hydrolysate is from 1:0.2 to 1:30.

7. The method according to claim 2, wherein the soybean protein hydrolysate is in the form of a protein hydrolysate/emulsifier complex.

8. The method according to claim 7, wherein the complex comprises at least 5% emulsifier on dry weight basis.

9. The method according to claim 2, wherein the plant sterol is in the form of a plant sterol/emulsifier complex or dissolved or suspended in fat or a mixture of fat and an emulsifier.

10. The method according to claim 2, wherein the soybean protein hydrolysate and the plant sterol are in the form of a protein hydrolysate/plant sterol/emulsifier complex.

11. The method according to claim 9, wherein the weight ratio of the plant sterol to emulsifier is from 1:0.01 to 1:5.

12. The method according to claim 2, wherein the fat content is from 0 to 80% of the weight of the complex or suspension or solution.

13. A method of lowering serum triglycerides in a subject in need thereof, comprising administering to the subject a food product comprising at least one basic nutritional ingredient and an oral therapeutical composition comprising a soybean protein hydrolysate and a plant sterol, wherein the weight ratio of the plant sterol to the soybean protein hydrolysate is from 1:0.02 to 1:150.

14. The method according to claim 13, wherein the food product is in the form of a product selected from the group consisting of bakery, confectionery, cereal, fermented cereal, snacks, beverage, dairy, sauce, soup, meat, fish, poultry, egg, soy based, vegetable oil based and ready mix products.

15. The method according to claim 14, wherein the plant sterol content calculated as sterol equivalents is from 0.05 to 20 g per 100 g food product and the soybean protein hydrolysate content is from 0.0002 to 20 g per 100 g food product.

16. The method according to claim 1, wherein the soybean protein hydrolysate is administrated at a rate of 0.1 to 60 g per day, and the plant sterol is administrated at a rate of 0.4 to 5 g per day calculated as sterol equivalents.

* * * * *